(12) United States Patent
Andrews (10) Patent No.: US 7,452,436 B2
(45) Date of Patent: Nov. 18, 2008

(54) TRANSVERSE TAPE APPLICATION METHOD AND APPARATUS

(75) Inventor: Robert E. Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 11/371,468

(22) Filed: Mar. 9, 2006

(65) Prior Publication Data

US 2006/0201619 A1    Sep. 14, 2006

Related U.S. Application Data

(60) Provisional application No. 60/659,785, filed on Mar. 9, 2005.

(51) Int. Cl.
| | |
|---|---|
| B29C 65/50 | (2006.01) |
| B29C 65/56 | (2006.01) |
| B32B 37/22 | (2006.01) |
| B44C 1/24 | (2006.01) |
| B65C 9/30 | (2006.01) |
| B32B 37/26 | (2006.01) |
| B44C 1/17 | (2006.01) |
| B65C 9/20 | (2006.01) |

(52) U.S. Cl. ............... 156/249; 156/238; 156/247; 156/469; 156/519; 156/571

(58) Field of Classification Search ............... 156/519, 156/521, 571, 65, 469, 230, 238, 241, 247
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |

(Continued)

FOREIGN PATENT DOCUMENTS

BE    1007854    11/1995

(Continued)

OTHER PUBLICATIONS

Reciprocating Mechanisms, Ingenious Mechanisms for Designers and Inventors, Franklin Jones vol. 1, 1930.

*Primary Examiner*—Philip C Tucker
*Assistant Examiner*—Sonya Mazumdar
(74) *Attorney, Agent, or Firm*—Ryan Kromholz & Manion S.C.

(57) ABSTRACT

A method and apparatus for applying tape tabs to a traveling web of material when the tape tabs are moving at a non-parallel angle to the web of material. An anvil that carries the tape tabs moves at a perpendicular or other non-parallel angle to the web. The invention allows placement of the tape tabs at different arrangements, such as the tape tabs running parallel to the web of material. A wheel with a protuberance located near the web contacts the web to press the web down and adhere a tape tap to the moving web.

10 Claims, 4 Drawing Sheets

U.S. PATENT DOCUMENTS

| | | |
|---|---|---|
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 6/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A * | 9/1971 | Berg et al. .................. 156/552 |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A * | 11/1974 | Blomqvist et al. .......... 156/511 |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A * | 2/1982 | Wilson ...................... 156/227 |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |

| | | | | | | |
|---|---|---|---|---|---|---|
| 4,589,945 | A | | 5/1986 | Polit | | |
| 4,603,800 | A | | 8/1986 | Focke et al. | | |
| 4,614,076 | A | | 9/1986 | Rathemacher | | |
| 4,619,357 | A | | 10/1986 | Radzins et al. | | |
| 4,634,482 | A | | 1/1987 | Lammers | | |
| 4,641,381 | A | | 2/1987 | Heran et al. | | |
| 4,642,150 | A | | 2/1987 | Stemmler | | |
| 4,642,839 | A | | 2/1987 | Urban | | |
| 4,650,530 | A | | 3/1987 | Mahoney et al. | | |
| 4,663,220 | A | | 5/1987 | Wisnecki et al. | | |
| 4,672,705 | A | | 6/1987 | Bors et al. | | |
| 4,675,062 | A | * | 6/1987 | Instance | ......... | 156/227 |
| 4,693,056 | A | | 9/1987 | Raszewski | | |
| 4,701,239 | A | * | 10/1987 | Craig | ......... | 156/519 |
| 4,726,874 | A | * | 2/1988 | VanVliet | ......... | 156/495 |
| 4,726,876 | A | | 2/1988 | Tomsovic et al. | | |
| 4,743,241 | A | | 5/1988 | Igaue et al. | | |
| 4,751,997 | A | | 6/1988 | Hirsch | | |
| 4,753,429 | A | | 6/1988 | Irvine et al. | | |
| 4,756,141 | A | | 7/1988 | Hirsch et al. | | |
| 4,764,325 | A | | 8/1988 | Angstadt | | |
| 4,765,780 | A | | 8/1988 | Angstadt | | |
| 4,776,920 | A | | 10/1988 | Ryan | | |
| 4,777,513 | A | | 10/1988 | Nelson | | |
| 4,782,647 | A | | 11/1988 | Williams et al. | | |
| 4,785,986 | A | | 11/1988 | Daane et al. | | |
| 4,795,510 | A | * | 1/1989 | Wittrock et al. | ......... | 156/64 |
| 4,801,345 | A | | 1/1989 | Dussaud et al. | | |
| 4,802,570 | A | | 2/1989 | Hirsch et al. | | |
| 4,840,609 | A | | 6/1989 | Jones et al. | | |
| 4,845,964 | A | | 7/1989 | Bors et al. | | |
| 4,864,802 | A | | 9/1989 | D'Angelo | | |
| 4,880,102 | A | | 11/1989 | Indrebo | | |
| 4,888,231 | A | | 12/1989 | Angstadt | | |
| 4,892,536 | A | | 1/1990 | Des Marais et al. | | |
| 4,904,440 | A | | 2/1990 | Angstadt | | |
| 4,908,175 | A | | 3/1990 | Angstadt | | |
| 4,909,019 | A | | 3/1990 | Delacretaz et al. | | |
| 4,925,520 | A | | 5/1990 | Beaudoin et al. | | |
| 4,927,322 | A | | 5/1990 | Schweizer et al. | | |
| 4,927,582 | A | | 5/1990 | Bryson | | |
| 4,937,887 | A | | 7/1990 | Schreiner | | |
| 4,963,072 | A | | 10/1990 | Miley et al. | | |
| 4,987,940 | A | | 1/1991 | Straub et al. | | |
| 4,994,010 | A | | 2/1991 | Doderer-Winkler | | |
| 5,000,806 | A | | 3/1991 | Merkatoris et al. | | |
| 5,021,111 | A | * | 6/1991 | Swenson | ......... | 156/264 |
| 5,025,910 | A | | 6/1991 | Lasure et al. | | |
| 5,045,039 | A | | 9/1991 | Bay | | |
| 5,062,597 | A | | 11/1991 | Martin et al. | | |
| 5,064,179 | A | | 11/1991 | Martin | | |
| 5,080,741 | A | | 1/1992 | Nomura et al. | | |
| 5,094,658 | A | | 3/1992 | Smithe et al. | | |
| 5,096,532 | A | | 3/1992 | Neuwirth et al. | | |
| 5,108,017 | A | | 4/1992 | Adamski et al. | | |
| 5,109,767 | A | | 5/1992 | Nyfeler et al. | | |
| 5,110,403 | A | | 5/1992 | Ehlert | | |
| 5,127,981 | A | | 7/1992 | Straub et al. | | |
| 5,131,525 | A | | 7/1992 | Musschoot | | |
| 5,147,487 | A | | 9/1992 | Nomura et al. | | |
| 5,163,594 | A | | 11/1992 | Meyer | | |
| 5,171,239 | A | | 12/1992 | Igaue et al. | | |
| 5,176,244 | A | | 1/1993 | Radzins et al. | | |
| 5,183,252 | A | | 2/1993 | Wolber et al. | | |
| 5,188,627 | A | | 2/1993 | Igaue et al. | | |
| 5,195,684 | A | | 3/1993 | Radzins | | |
| 5,203,043 | A | | 4/1993 | Riedel | | |
| 5,213,645 | A | | 5/1993 | Nomura et al. | | |
| 5,223,069 | A | | 6/1993 | Tokuno et al. | | |
| 5,226,992 | A | | 7/1993 | Morman | | |
| 5,246,433 | A | | 9/1993 | Hasse et al. | | |
| 5,267,933 | A | | 12/1993 | Precoma | | |
| 5,308,345 | A | | 5/1994 | Herrin | | |
| 5,328,438 | A | | 7/1994 | Crowley | | |
| 5,340,424 | A | | 8/1994 | Matsushita | | |
| 5,368,893 | A | | 11/1994 | Sommer et al. | | |
| 5,407,513 | A | | 4/1995 | Hayden et al. | | |
| 5,415,649 | A | | 5/1995 | Watanabe et al. | | |
| 5,421,924 | A | | 6/1995 | Ziegelhoffer et al. | | |
| 5,424,025 | A | | 6/1995 | Hanschen et al. | | |
| 5,429,576 | A | * | 7/1995 | Doderer-Winkler | ......... | 493/214 |
| 5,435,802 | A | | 7/1995 | Kober | | |
| 5,449,353 | A | | 9/1995 | Watanabe et al. | | |
| 5,464,401 | A | | 11/1995 | Hasse et al. | | |
| 5,486,253 | A | | 1/1996 | Otruba | | |
| 5,494,622 | A | | 2/1996 | Heath et al. | | |
| 5,531,850 | A | * | 7/1996 | Herrmann | ......... | 156/161 |
| 5,540,647 | A | | 7/1996 | Weiermann et al. | | |
| 5,545,275 | A | | 8/1996 | Herrin et al. | | |
| 5,545,285 | A | | 8/1996 | Johnson | | |
| 5,552,013 | A | | 9/1996 | Ehlert et al. | | |
| 5,556,360 | A | | 9/1996 | Kober et al. | | |
| 5,556,504 | A | | 9/1996 | Rajala et al. | | |
| 5,560,793 | A | | 10/1996 | Ruscher et al. | | |
| 5,602,747 | A | | 2/1997 | Rajala | | |
| 5,624,420 | A | | 4/1997 | Bridges et al. | | |
| 5,624,428 | A | | 4/1997 | Sauer | | |
| 5,628,738 | A | | 5/1997 | Suekane | | |
| 5,634,917 | A | | 6/1997 | Fujioka et al. | | |
| 5,643,165 | A | | 7/1997 | Klekamp | | |
| 5,643,396 | A | | 7/1997 | Rajala et al. | | |
| 5,645,543 | A | | 7/1997 | Nomura et al. | | |
| 5,659,229 | A | | 8/1997 | Rajala | | |
| 5,660,657 | A | | 8/1997 | Rajala et al. | | |
| 5,660,665 | A | | 8/1997 | Jalonen | | |
| 5,683,376 | A | | 11/1997 | Kato et al. | | |
| RE35,687 | E | | 12/1997 | Igaue et al. | | |
| 5,693,165 | A | | 12/1997 | Schmitz | | |
| 5,699,653 | A | | 12/1997 | Hartman et al. | | |
| 5,707,470 | A | | 1/1998 | Rajala et al. | | |
| 5,711,832 | A | | 1/1998 | Glaug et al. | | |
| 5,725,518 | A | | 3/1998 | Coates | | |
| 5,745,922 | A | | 5/1998 | Rajala et al. | | |
| 5,746,869 | A | * | 5/1998 | Hayden et al. | ......... | 156/265 |
| 5,749,989 | A | | 5/1998 | Linman et al. | | |
| 5,788,797 | A | | 8/1998 | Herrin et al. | | |
| 5,817,199 | A | | 10/1998 | Brennecke et al. | | |
| 5,829,164 | A | | 11/1998 | Kotitschke | | |
| 5,836,931 | A | | 11/1998 | Toyoda et al. | | |
| 5,858,012 | A | | 1/1999 | Yamaki et al. | | |
| 5,865,393 | A | | 2/1999 | Kreft et al. | | |
| 5,868,727 | A | | 2/1999 | Barr et al. | | |
| 5,876,027 | A | | 3/1999 | Fukui et al. | | |
| 5,876,792 | A | | 3/1999 | Caldwell | | |
| 5,879,500 | A | | 3/1999 | Herrin et al. | | |
| 5,902,431 | A | | 5/1999 | Wilkinson | | |
| 5,932,039 | A | | 8/1999 | Popp et al. | | |
| 5,938,193 | A | | 8/1999 | Bluemle et al. | | |
| 5,964,970 | A | | 10/1999 | Woolwine et al. | | |
| 6,036,805 | A | | 3/2000 | McNichols | | |
| 6,043,836 | A | | 3/2000 | Kerr et al. | | |
| 6,050,517 | A | | 4/2000 | Dobrescu et al. | | |
| 6,074,110 | A | | 6/2000 | Verlinden et al. | | |
| 6,076,442 | A | | 6/2000 | Arterburn et al. | | |
| 6,098,249 | A | | 8/2000 | Toney et al. | | |
| 6,123,792 | A | | 9/2000 | Samida et al. | | |
| 6,183,576 | B1 | | 2/2001 | Couillard et al. | | |
| 6,210,386 | B1 | | 4/2001 | Inoue | | |
| 6,212,859 | B1 | | 4/2001 | Bielik, Jr. et al. | | |
| 6,250,048 | B1 | | 6/2001 | Linkiewicz | | |
| 6,264,784 | B1 | | 7/2001 | Menard et al. | | |
| 6,276,421 | B1 | | 8/2001 | Valenti et al. | | |
| 6,306,122 | B1 | | 10/2001 | Narawa et al. | | |
| 6,309,336 | B1 | | 10/2001 | Muessig et al. | | |
| 6,312,420 | B1 | | 11/2001 | Sasaki et al. | | |
| 6,314,333 | B1 | | 11/2001 | Rajala et al. | | |

| | | |
|---|---|---|
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1* | 11/2002 | Parrish et al. .............. 156/265 |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1* | 2/2003 | Hilt et al. ................... 156/265 |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,684,925 B2* | 2/2004 | Nagate et al. .............. 156/540 |
| 6,766,817 B2 | 7/2004 | da Silva |
| D497,991 S | 11/2004 | Otsubo et al. |
| 6,820,671 B2* | 11/2004 | Calvert ....................... 156/543 |
| 6,837,840 B2 | 1/2005 | Yonekawa et al. |
| 6,840,616 B2 | 1/2005 | Summers |
| 6,852,186 B1* | 2/2005 | Matsuda et al. ............. 156/230 |
| 6,875,202 B2 | 4/2005 | Kumasaka et al. |
| 6,893,528 B2* | 5/2005 | Middelstadt et al. ........ 156/264 |
| 6,918,404 B2 | 7/2005 | Dias da Silva |
| 6,978,486 B2* | 12/2005 | Zhou et al. ..................... 2/400 |
| 7,066,586 B2 | 6/2006 | da Silva |
| 7,077,393 B2 | 7/2006 | Ishida |
| 7,172,666 B2 | 2/2007 | Groves et al. |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1* | 8/2001 | Otruba et al. ................. 156/64 |
| 2002/0046802 A1 | 4/2002 | Tachibana et al. |
| 2002/0059013 A1 | 5/2002 | Rajala et al. |
| 2003/0000620 A1 | 1/2003 | Herrin et al. |
| 2003/0015209 A1 | 1/2003 | Gingrass et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0112517 A1 | 6/2004 | Groves et al. |
| 2004/0164482 A1 | 8/2004 | Edinger |
| 2005/0000628 A1 | 1/2005 | Norrley |
| 2005/0196538 A1 | 9/2005 | Sommer et al. |
| 2005/0230056 A1* | 10/2005 | Meyer et al. ................ 156/517 |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0025130 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 03040140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 0206208 | 12/1986 |
| FR | 2891811 | 4/2007 |
| GB | 191101501 | 1/1911 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 1/1998 |
| JP | 10-277091 | 12/1998 |
| SE | 0602047 | 5/2007 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO05075163 | 1/2005 |

* cited by examiner

TRANSVERSE TAPE APPLICATION METHOD AND APPARATUS

RELATED APPLICATION

This application claims the benefit of U.S. Provisional Patent Application Ser. No. 60/659,785, filed 9 Mar. 2005, and entitled "Transverse Tape Application Method and Apparatus."

BACKGROUND OF THE INVENTION

The present invention relates to processes and apparatus for applying tabs to traveling webs, and more specifically to application of multiple tabs to a traveling web. The invention has particular applicability to the manufacture of disposable diapers.

The history of cutting and applying tape tabs to disposable diaper webs is now entering its fourth decade. Over the course of that time, various types of automatic manufacturing equipment have been developed which produce the desired results with a variety of materials and configurations. This equipment generally included window-knife and slip-and-cut applicators, each having their own advantages and limitations.

Window-knife applicators are comprised of: one or more rotating heads, each made up of a knife edge and a vacuum plate; a more or less stationary knife, which is configured with a hole (window); and a tape transfer mechanism. Typically, the rotating heads are mechanically configured so as to eliminate head rotation relative to the stationary knife. Each head is passed, once per cycle, across the face of the stationary window knife, through which the infeeding tape is passed. The rotating knife shears the extended length of tape against the sharp inner edge of the hole (window), after which the severed segment is held by the vacuum plate. The rotating head, with the segment of tape held in place by the vacuum plate, continues through its rotation to a point, usually 90 degrees later, where it contacts the traveling web, which is pressed against the exposed adhesive of the tape segment. This contact, usually against some backing device, effects a transfer of the tape tab from the vacuum plate to the traveling web, which then carries the tape tab downstream.

Window-knife applicators have a few shortcomings, among which are: the difficulty in feeding tape webs with little axial stiffness; the tendency of the infeeding tape to adhere to the window knife-edge; and for exposed adhesive to contaminate the surfaces of the window knife. For effective cutting, some degree of interference between the cutting edges is necessary between the moving and stationary knife faces, so to minimize impact, precision in manufacturing must be maintained and provision must be made for a degree of resiliency. While applicators of this type have been tested to speeds of 1000 cuts per minute, the maximum practical speed capability of current designs is approximately 750 cuts per minute.

Slip-and-cut applicators are typically comprised of (a) a cylindrical rotating vacuum anvil (b) a rotating knife roll and (c) a transfer device. In typical applications, a tape web is fed at a relatively low speed along the vacuum face of the rotating anvil, which is moving at a relatively higher surface speed and upon which the tape web is allowed to "slip". A knife-edge, mounted on the rotating knife roll, cuts a segment of tape from the tape web against the anvil face. This knife-edge is preferably moving at a surface velocity similar to that of the anvil's circumference. Once cut, the tape tab is held by vacuum drawn through holes on the anvil's face as it is carried at the anvil's speed downstream to the transfer point where the tape segment is transferred to the traveling web.

A common problem with slip-and-cut applicators lies in the tendency to accumulate various contaminants on their anvil surfaces. This is most frequently seen in the form of the release compounds found on the non-adhesive side of tape, which is shipped on pre-wound rolls. Where die-cut tapes are fed onto the surfaces of slip-and-cut applicators, it is common to also see an accumulation of adhesive contamination, as the adhesive has been exposed at the tape edges by the die-cutting process. The difference in speed between the tape web and the anvil tends to "wipe" adhesive from the tape web. Contamination of the anvil, whether by release compounds or by fugitive adhesive, interferes with the regularity of slip occurring between the tape and the anvil, causing registration and cut accuracy problems. Frequent cleaning is necessary to maintain any level of productivity.

Another problem associated with slip-and-cut applicators occurs at the point of cut. Since the web being cut is traveling at a very low velocity compared to the anvil and knife velocity (perhaps 1/20th), the engagement of the knife with the tape web tends to induce a high tensile strain in the tape web. Having been placed under such a high level of stress, the tape web can recoil violently when the cut is finally completed, causing loss of control of the tape web. This "snap-back" effect increases with the thickness of the tape web. Thicker webs tend to prolong the duration of engagement with the knife before completion of the cut, thereby increasing the build-up of strain. This is a common process problem that is usually addressed by the provision of various shock-absorbing devices. One possible solution might have been to reduce the surface velocity of the knife, but substantially different velocities between the knife and anvil result in rapid wear of the knife edge and/or anvil face, depending on relative hardness.

Continual improvements and competitive pressures have incrementally increased the operational speeds of disposable diaper converters. As speeds increased, the mechanical integrity and operational capabilities of the applicators had to be improved accordingly. As a further complication, the complexity of the tape tabs being attached has also increased. Consumer product manufacturers are offering tapes which are die-cut to complex profiles and which may be constructed of materials incompatible with existing applicators. For instance, a proposed tape tab may be a die-profiled elastic textile, instead of a typical straight-cut stiff-paper and plastic type used in the past. Consequently, a manufacturer may find itself with a window-knife applicator, which cannot feed a tape web with too little axial stiffness. It could also find itself with a slip-and-cut applicator, which cannot successfully apply die-cut tape segments. Furthermore, existing applicators cannot successfully apply tapes whose boundaries are fully profiled, as may be desired to eliminate sharp corners, which might irritate a baby's delicate skin. This demonstrates a clear need for an improved applicator capable of applying new tape configurations and overcoming other shortcomings of some prior art applicators.

To overcome these shortcomings, Parish et al. (U.S. Pat. No. 6,475,325), which has been assigned to the same assignee as the present application, discloses an applicator and method that allows tape tabs to be applied to a running web of material, even when the web of tape tab material is moving at a different speed than the web of material. A protuberance acting against the web of material brings the web into contact with the tape tabs and adheres the tape tabs to the web. While this invention adequately solved many of the problems of the prior art, it did not address the placement of tape tabs which are being fed at a non-parallel angle to the web of material.

SUMMARY OF THE INVENTION

The present invention has the added capability over the prior art of applying tape tabs to a running web of material at non-parallel feed positions.

The invention provides the additional benefit of quiet operation compared to prior art equipment, which uses high speed cutting faces and suffers from the effects of the very high energy levels seen at the point of contact. Generally, these energies, and the sounds that they generate, increase in proportion to the square of the velocity. The present invention benefits from the relatively low speed of the cutting faces and exhibits extremely low noise levels. In fact, the underlying noise of the mechanical drive systems and the traveling web equipment contribute to make the cutting noise level nearly unnoticeable.

The present invention provides a simplified process wherein a rotary knife or die, with one or more cutting edges, turns against and in coordination with a corresponding vacuum anvil cylinder. An infeeding tape web is fed along the surface of the anvil, which is rotating at a surface velocity equal to or only somewhat greater than that of the tape web. As the tape web passes the nip created between the knife-edges and the anvil surface, segments of tape are parted but not significantly displaced upon the anvil surface. The segments continue downstream on the anvil surface, held securely by forces induced by a vacuum source directed to one or more holes provided for each segment in the anvil surface.

At a point downstream along the surface of the anvil, the traveling web to which the segments are to be attached is brought into close proximity with the anvil and its tape segments. The traveling web is proceeding at a non-parallel angle and direction to the rotational direction of the anvil. A mechanically operated device, which may be as simple as a protuberance on a rotating cylinder, presses the target zone of the traveling web against the exposed adhesive of the tape segment as it is presented on the anvil surface. The protuberance preferably has a surface velocity substantially identical to that of the traveling web.

Given the extremely low moment of inertia of the tape segments and the aggressive adhesion provided between its exposed adhesive and the compatible surface of the traveling web, each successive segment is successfully transferred to the traveling web, accelerating almost instantly to the speed of the traveling web.

A key aspect of this invention lies in the method and apparatus used to affect the transfer of the tape segments from the anvil to the traveling web. In accordance with the invention, a vacuum commutation system is configured to remove or reduce the level of vacuum used to hold each tape segment to the anvil surface just before the point of transfer. The materials and finishes selected for the anvil and the transfer protuberances provide a situation in which the coefficient of friction between the protuberances and the traveling web is relatively high, while the coefficient of friction between the tape segment and the anvil is relatively low. The highly aggressive nature of the bond between the adhesive side of the tape segment and the target surface of the traveling web ensures that there is virtually no slippage between the two. This ensures that the traveling web is driven through the point of transfer at its existing velocity, and that any tendency of the tape segment to adhere to the anvil surface will not influence the traveling web. The process requires that some slip occurs, and in accordance with the invention, slip occurs only between the tape segment and the anvil surface.

The present invention allows for placement of tape onto areas of the disposable garment perpendicular to or at another non-parallel angle to the waistband of the disposable garment. For instance, training pants for babies typically have a removable panel in the rear of the diaper. A soiled panel is removed from the pants and rolled up and secured with the fastening tapes. The present invention provides for a method to apply the transverse fastening tapes to the diaper. Likewise, the present invention provides a method to attach tapes to the sides of garments that are manufactured according to a transverse process.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
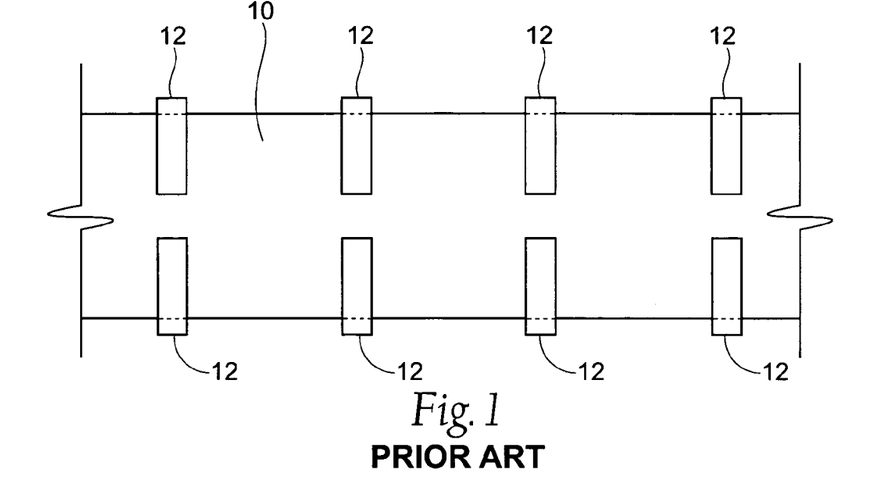
FIG. 1 is an overhead diagrammatic view of tape being applied according to the prior art.

FIG. 1 shows an overhead view of a web of traveling material 10 having tape tabs 12 applied to the web 10 according to the prior art. The tape tabs 12 are applied from an anvil carrying an adhesive material (not shown) that rotates in the same direction as the movement of the web 10. The tabs 12 are placed so that the tabs 12 are attached perpendicular to the web 10.

Figure 2:
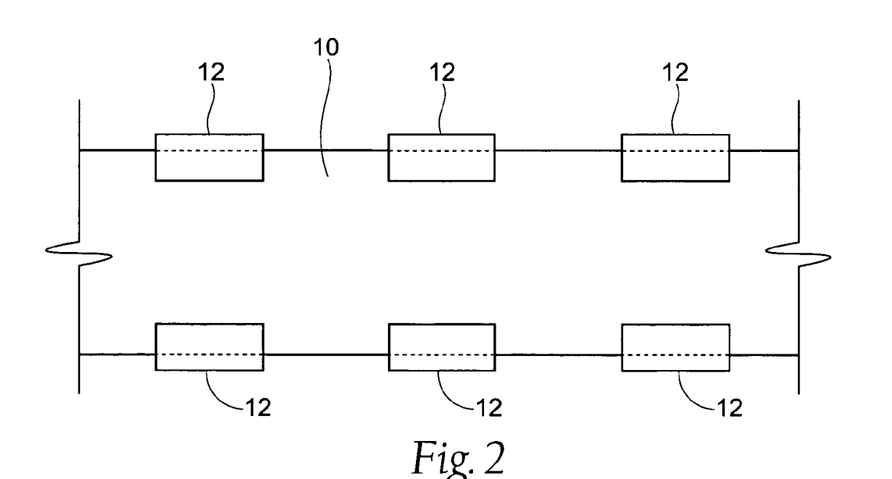
FIG. 2 is an overhead diagrammatic view of tape being applied according to the present invention.

FIG. 2 is an overhead view of the improvement of the present invention. The tabs 12 are attached parallel to the moving web 10. The change in orientation is possible since an anvil that carries the adhesive tape 12 rotates in a direction perpendicular to the moving web 10. The advantages of such an arrangement will be discussed later. Two separate anvils contacting the web 10 apply the tape 12, with one anvil coming in contact with each edge of the web 10.

Figure 3:
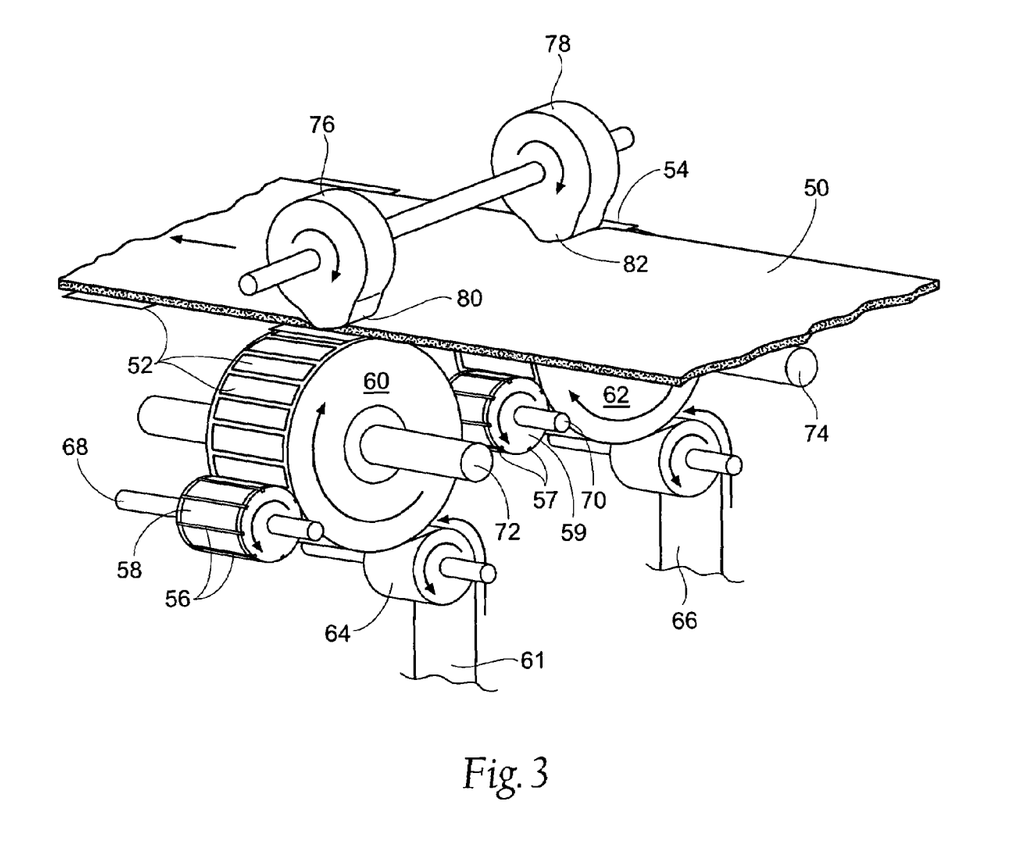
FIG. 3 is a perspective view illustrating an embodiment of the invention.

In FIG. 3 there is shown, a simplified device in accordance with the invention, illustrating the application of tabs 52 and 54, which have free ends extending parallel from opposite sides of a diaper-forming web 50. These free ends of tabs 52 and 54 may be provided with loops on one side of the diaper-forming material and hooks on the opposite side to form hook and loop fasteners on the diapers commonly referred to as Velcro®. In other cases, the tabs on at least one side may be coated with a pressure sensitive adhesive protected until use by a release layer.

As further seen in FIG. 3, an adhesive-coated tape web 61 is fed over a roller 64 onto an anvil 60. The web 61 is fed to the anvil 60 at a speed such that the web speed of web 61 approximately equals the speed at which the outer periphery of anvil 60 is traveling. If desired, the anvil 60 may rotate at a slightly higher speed than the linear speed of the web 61. Blades 56 of a rotary cutter 58 are also traveling at a peripheral speed equal to that of anvil 60. As seen in FIG. 3, after cutting, a series of tabs 52 are carried on the outer surface of anvil 60. Tabs 52 are held in place by vacuum provided within the interior of anvil 60. The adhesive-coated surface of web 61 is facing outwardly while a non-tacky or uncoated surface engages the exterior anvil 60.

A similar anvil 62 engages a second adhesive-coated web 66. The webs 61 and 66 may have adhesive coated on one-half of their width and a hook or loop-type fastener provided on the opposite half of the width in order to form the laterally extending tabs 52 and 54. Blades 56 of rotary cutter 58 and blades 57 of a second rotary cutter 59 cut the webs 61 and 66, respectively. The cutters 58 and 59 are driven by respective rotatable shaft 68 and 70. Similarly, anvils 60 and 62 are driven by respective central shaft 72 and 74. Rotatable disks 76 and 78 provided with protrusions 80 and 82 serve to deflect the edges of the web 50 toward the respective anvils 60 and 62 in order to simultaneously pick up the tabs 54 and 52 on opposite sides of the web 50, as shown.

Figure 4:
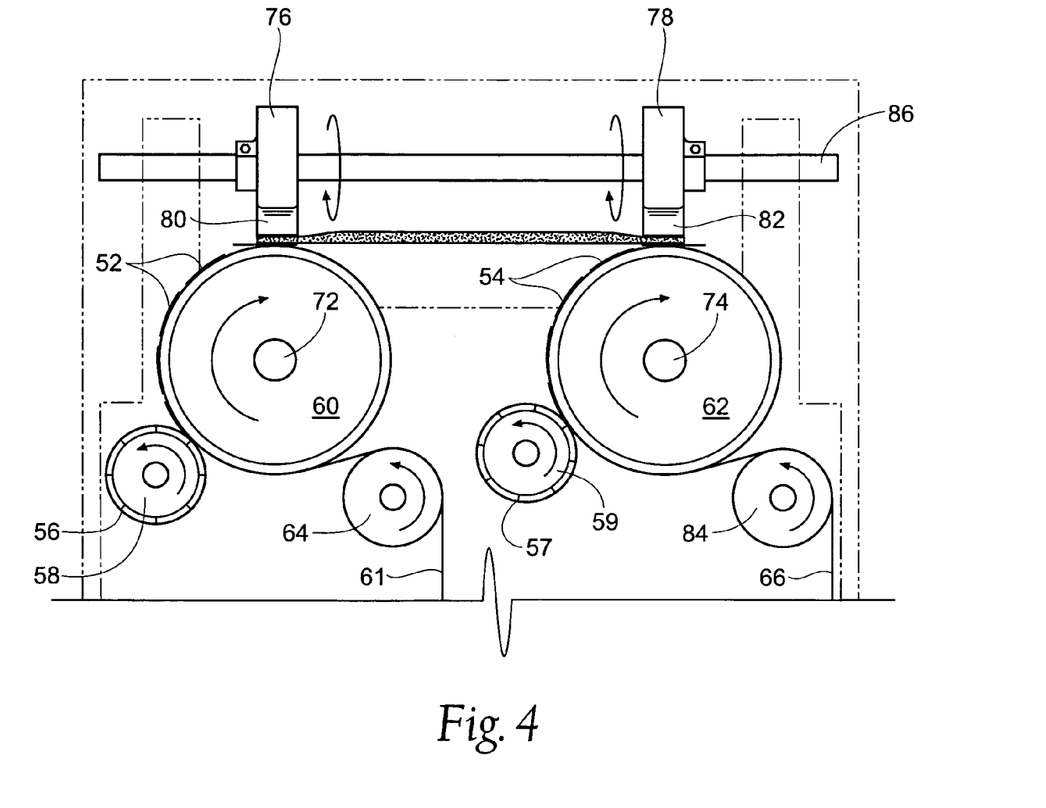
FIG. 4 is a front elevational view of the equipment of FIG. 3.

FIG. 4 shows a front elevation view of the apparatus of FIG. 3. The incoming webs 61 and 66 are fed to the rollers 64 and 84. The webs 61 and 66 travel further to come into contact with the anvils 60 and 62. The webs 61 and 66 are fed to the anvils 60 and 62 at a speed such that the web speed of the webs 61 and 66 approximately equals the speed at which the outer periphery of 60 and 62 are traveling. If desired, the anvils 60 and 62 may rotate at a slightly higher speed than the linear speed of the webs 61 and 66. The blades 56 and 57 of the rotary cutters 58 and 59 are also traveling at a peripheral speed equal to that of anvils 60 and 62. As seen in FIG. 4, after cutting, a series of tabs 52 and 54 are carried on the outer surfaces of the anvils 60 and 62. Tabs 52 and 54 are held in place by vacuum provided within the interiors of anvils 60 and 62. The adhesive-coated surface of the webs 61 and 66 are facing outwardly while a non-tacky or uncoated surface engages the exterior of the anvils 60 and 62.

The web 50 of diaper material is caused to travel in a path slightly displaced from the outer surface of the rotating anvils 60 and 62, but in close proximity thereto. Just above the web 10 the rotating wheels 76 and 78, which rotates at a peripheral velocity equal to the lineal velocity of web 50, which, in turn, is substantially greater than the peripheral velocity of the anvils 60 and 62. The anvils 60 and 62 may travel at a peripheral velocity either equal to or somewhat greater than the velocity of web 50. In practice, to realize the benefits of this invention, the peripheral velocity of anvils 60 and 62 should not be greater than about 5 times the velocity of web 50.

As the tabs 52 and 54 travel toward the web 50, the protrusions 80 and 82 located on the wheels 76 and 78 depress the web 50, causing the web 50 to come into contact with the anvils 60 and 62, which adheres the tabs 52 and 54 to the web 50.

As shown in FIG. 4, a shaft 86 that controls the wheels 76 and 78 is aligned perpendicular to the shafts 72 and 74, which allows the tabs 52 and 54 to be placed in the parallel fashion shown in FIG. 3. While the invention is shown having one protrusion 80 and 82 on each wheel 76 and 78, the invention may also be used having two or more protrusions located on the wheels. Likewise, the invention may be used with only one wheel instead of two. The anvils 60 and 62 are shown rotating in the same direction, but it may be possible to arrange the anvils so that they are rotating in opposite directions if preferred, thereby allowing the same relative edges of the tabs 52 and 54 to be placed on the web 50 in the same manner.

Figure 5:
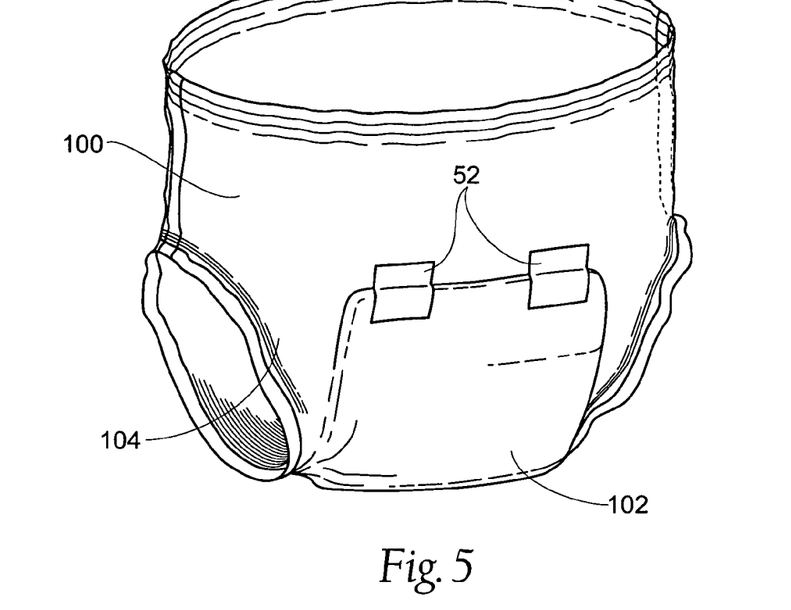
FIG. 5 is a perspective view of the present invention applied to an undergarment.

For instance, as shown in FIG. 5, a disposable undergarment 100 is considered. The garment 100 has a releasable flap 102 located on the rear 104 of the undergarment 100. The present invention allows placement of the tabs 52 onto the flap 102 in a parallel fashion, which allows the flap 102 to be opened or closed. Such an arrangement is useful for children to check if the undergarment 100 has been soiled. If the undergarment 100 has been soiled, the arrangement allows for the soiled flap 102 to be rolled up and secured with the tabs 52.

Figure 6:
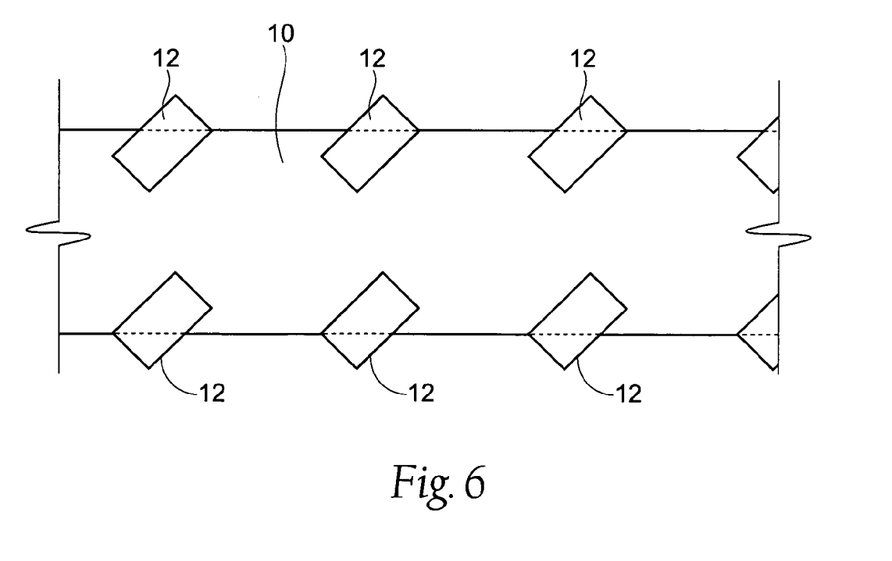
FIG. 6 is an overhead diagrammatic view of an alternate embodiment of the present invention.

The invention has also been contemplated where adhesive may be placed onto a web that is not perpendicular to the web of material. FIG. 6 represents a diagrammatic view of such an arrangement. The tabs 12 are placed onto the web of material 10 at approximately a 45E angle. The angle may adjusted so that the tabs 12 may be placed on the web 10 so that the tabs 12 may lie between any angle parallel to perpendicular to the traveling web 10.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A method of applying a tab to a traveling web, the method comprising:
   rotating a pair of drums about a pair of stationary first axes, each of said drums carrying a tab;
   providing a target web for receiving said tabs, said target web traveling in a direction substantially parallel to said pair of stationary first axes; and
   urging at least one fixed axis protuberance against said target web to urge said target web into contact with said tabs, said tabs coupling with said traveling web, said fixed axis protuberance rotated into contact with said target web about a stationary second axis, said stationary second axis skew to said pair of stationary first axes.

2. The method of claim 1, wherein said tabs are coupled to said traveling web by an adhesive.

3. The method of claim 2, wherein said adhesive is carried by said tabs.

4. The method of claim 1, wherein said at least one protuberance is carried by a wheel.

5. A method of applying a tab to a traveling web, the method comprising:
   rotating a pair of drums about a pair of stationary first axes, each of said drums carrying a tab;
   providing a target web for receiving said tabs, said target web traveling in a direction that is oblique to said pair of first axes; and
   urging at least one fixed axis protuberance against said target web to urge said target web into contact with said tabs, said tabs coupling with said traveling web.

6. The method of claim 5, wherein said tabs are coupled to said traveling web by an adhesive.

7. The method of claim 6, wherein said adhesive is carried by said tabs.

8. The method of claim 5, wherein said at least one protuberance is rotated into contact with said target web.

9. The method of claim 5, wherein said at least one protuberance is carried by a wheel.

10. The method of claim 5, wherein the step of urging the at least one protuberance comprises rotating said at least one protuberance about a second axis, wherein said second axis is skew to said pair of first axes.

* * * * *